US008017576B2

(12) United States Patent
Toback (10) Patent No.: US 8,017,576 B2
(45) Date of Patent: Sep. 13, 2011

(54) METHODS AND COMPOSITIONS TO TREAT MUCOSITIS

(75) Inventor: F. Gary Toback, Chicago, IL (US)

(73) Assignee: The University of Chicago, Chicago, IL (US)

(*) Notice: Subject to any disclaimer, the term of this patent is extended or adjusted under 35 U.S.C. 154(b) by 522 days.

(21) Appl. No.: 11/913,928

(22) PCT Filed: May 9, 2006

(86) PCT No.: PCT/US2006/018014
§ 371 (c)(1),
(2), (4) Date: Dec. 12, 2007

(87) PCT Pub. No.: WO2006/122162
PCT Pub. Date: Nov. 16, 2006

(65) Prior Publication Data
US 2008/0194479 A1  Aug. 14, 2008

Related U.S. Application Data

(63) Continuation of application No. 60/790,177, filed on Apr. 7, 2006.

(30) Foreign Application Priority Data

May 10, 2005  (EP) .................................... 05010217

(51) Int. Cl.
*A61K 38/10* (2006.01)
*A61K 38/18* (2006.01)
(52) U.S. Cl. ....... 514/7.6; 514/13.2; 514/21.4; 514/21.5
(58) Field of Classification Search .................. None
See application file for complete search history.

(56) References Cited

U.S. PATENT DOCUMENTS

| 5,102,870 | A * | 4/1992 | Florine et al. .................... 514/12 |
| 5,644,026 | A | 7/1997 | Yamaguchi et al. |
| 6,670,119 | B1 | 12/2003 | Yoshikawa et al. |
| 6,734,289 | B2 | 5/2004 | Martin et al. |
| 6,913,919 | B2 | 7/2005 | Botstein et al. |
| 2005/0031582 | A1 | 2/2005 | Toback et al. |
| 2005/0054564 | A1 | 3/2005 | Martin et al. |

FOREIGN PATENT DOCUMENTS

| EP | 0972830 A1 | 1/2000 |
| WO | WO 98/37187 A1 | 8/1998 |
| WO | WO 99/07840 A1 | 2/1999 |
| WO | WO 00/00610 A2 | 1/2000 |
| WO | WO 00/43781 A2 | 7/2000 |
| WO | WO 00/73348 A2 | 12/2000 |
| WO | WO 02/078640 A2 | 10/2002 |

OTHER PUBLICATIONS

Database Biosis: Walsh-Reitz et al., "Accumulation of Specific Tight and Adherens Junction Proteins is Stimulated by Antrum Mucosal Protein-18 in Colonic Epithelial Cells in Culture and Mouse In Vivo," Database Accession No. PREV200300571862, Abstract (2003).
Martin et al., "A Novel Mitogenic Protein That is Highly Expressed in Cells of the Gastric Antrum Mucosa," *American Journal of Physiology: Gastrointestinal and Liver Physiology*, 285: (2), G332-G343 (2003).
Toback et al., "Peptide Fragments of AMP-18, A Novel Secreted Gastric Antrum Mucosal Protein, Are Mitogenic and Motogenic," *American Journal of Physiology: Gastrointestinal and Liver Physiology*, 285: (2), G344-G353 (2003).
International Search Report issued in PCT/US2006/018014 (2007).
Aithal et al., "Glyceraldehyse-3-phosphate Dehydrogenase Modifier Protein is Associated with Microtubules in Kidney Epithelial Cells," *Am. J. Physiol.*, 266, F612-619 (1994).
Altschul et al., "Gapped BLAST and PSI-BLAST: a New Generation of Protein Database Search Programs," *Nuc. Acids Res.*, 25 (17): 3389-3402 (1997).
Baczako et al., "Lectin-Binding Properties of the Antral and Body Surface Mucosa in the Human Stomach—Are Difference Relevant for Helicobacter Pylon Affinity," *J. Pathol.*, 176, 77-86 (1995).
Blaser, "Gastric Campylobacter-like Organisms, Gastritis, and Peptic Ulcer Disease," *Gastroenterol.*, 93, 371-383 (1987).
Boman, "Peptide Antibiotics and Their Role in Innate Immunity," *Ann. Rev. Immunol.*, 13, 16-92 (1995).
Clackson et al., "A Hot Spot of Binding Energy in a Hormone-Receptor Interface," *Science*, 267, 383-386 (1995).
Cohen et al., "Molecular Binding Domains in Signal Transduction Proteins," *Cell*, 80: 237-248 (1995).
Cregg et al., "Recent Advances in the Expression of Foreign Genes in *Pichia pastoris*," *Bio/Technol.*, 11, 905-910 (1993).
Database EMBL (2000): "Human Signal Peptide Containing Protein HSPP-40 SEQ ID No. 49," Accession No. AAY87272.
Database EMBL (2001): "Human PRO1005 (UNQ489) protein sequence SEQ ID No. 211," Accession No. AAB65209.
Database EMBL (2001): "*Mus musculus* Adult Male Stomach cDNA, RIKEN Full-Length Enriched Library, Clone: 2210420L15 Product: Weakly Similar to CA11 Protein [*Homo sapiens*], Full Insert Sequence," Accession No. AK008990.
Database EMBL (2001): "Sequence 14 From Patent WO0073348," Accession No. AX055699.
Dignass et al., "Adenine Nucleotides Modulate Epithelial Wound Healing In Vitro," *Eur. J. Clin. Invest.*, 28: 554-561 (1998).
Falk et al., "An In vitro Adherence Assay Reveals That *Helicobacter pylori* Exhibits Cell Lineage-Specific Tropism in the Human Gastric Epithelium," *Eur. J. Clin. Invest.*, 28: 554-561 (1993).
Goodwin et al., "*Campylocbacter pyloridis*, Gastritis, and Peptic Ulceration," *J. Clin. Pathol.*, 39: 353-356 (1986).
Hasty et al., "The Length of Homology Required for Gene Targeting in Embryonic Stem Cells," *Mol. Cell. Biol.*, 11: 5586-5591 (1991).
Houston et al., "Lactam Bridge Stabilization of alpha-Helices: The Role of Hydrophobicity in Controlling Dimeric versus Monomeric alpha-Helices," *Biochem.*, 35: 10041-10050 (1996).
Huang et al., "Transforming Growth Factor Beta Peptide Antagonists and Their Conversion to Partial Agonists," *The Journal of Biological Chemistry*, 272: (43), 27155-27159 (1997).

(Continued)

*Primary Examiner* — Jeffrey E Russel
(74) *Attorney, Agent, or Firm* — Barnes & Thornburg LLP; Alice O. Martin (57) ABSTRACT

Methods and compositions of AMP-18 derived peptides enablingly demonstrate that AMP-18 derived peptide compositions surprisingly reduce mucositis in mammals. Methods and peptide compositions treat mucositis, delays the onset or duration of mucositis, including cancer therapy-induced mucositis are disclosed. AMP 77-97 peptide derived from human AMP-18 protein alleviates cancer therapy-induced mucositis.

11 Claims, 6 Drawing Sheets

OTHER PUBLICATIONS

Janknecht et al., "Rapid and Efficient Purification of Native Histidine-Tagged Protein Expressed by Recombinant Vaccinia Virus," *Proc. Nat. Acad. Sci. USA*, 88: 8972-8976 (1991).

Jeon et al., "The Transcription Factor TFIIS Zinc Ribbon Dipeptide Asp-Glu is Critical for Stimulation of Elongation and RNA Cleavage by RNA Polymerase II," *Proc. Nat. Acad. Sci. USA*, 91: 9106-9110 (1994).

Johnson et al., "Microscopic Structure of Pyloric Epithelium of the Cat," *J. Anat.*, 107: 67-86 (1970).

Kartha et al., "Purine Nucleotides Stimulate DNA Synthesis in Kidney Epithelial Cells in Culture," *Am. J. Physiol.*, 249: F967-F972 (1985).

Kawai et al., "Functional Annotation of a Full-Length Mouse cDNA Collection," *Nature*, 409, 685-690 (2001).

Lacy, "Epithelial Restitution in the Gastrointestinal Tract," *J. Clin. Gastroenterol.*, 10 (Suppl. 1): s72-s77 (1998).

Lieske et al., "Renal Epithelial Cells Rapidly Bind and Internalize Calcium Oxalate Monohydrate Crystals," *Proc. Natl. Acad. Sci. USA*, 91: 6987-6991 (1994).

Lieske et al., "Adhesion of Hydroxyapatite Crystals to Anionic Sites on the Surface of Renal Epithelial Cells," *Am. J. Physiol.*, 273: F224-F233 (1997).

Mansour et al., "Disruption of the Proto-Oncogene *int*-2 in Mouse Embryo-Derived Stem Cells: A General Strategy for Targeting Mutations to Non-Selectable Genes," *Nature*, 336: 348-352 (1988).

Moore et al., "Antimicrobial Peptides in the Stomach of *Xenpus laevis*," *J. Biol. Chem.*, 266 (2a): 19851-19857 (1991).

Nguyen et al., "Exploiting the Basis of Proline Recognition by SH3 and WW Domains: Design of N-Substituted Inhibitors," *Science*, 282: 2088-2092 (1998).

Nomura et al., "*Helicobacter Pylori* Infection and Gastric Carcinoma Among Japanese Americans in Hawaii," *N. Engl. J. Med.*, 325 (16): 1132-1136 (1991).

Nusrat et al., "Intestinal Epithelial Restitution," *J. Clin. Invest.*, 89: 1501-1511 (1992).

Park et al., "A Novel Antimicrobial Peptide from the Loach, *Misgurnus anguillicaudatus*," *FEBS Lett.*, 411: 173-178 (1997).

Parsonnet et al., "*Helicobacter Pylori* Infection of the Risk of Gastric Carcinoma," *N. Engl. J. Med.*, 325 (16): 1127-1131 (1991).

Podolsky et al., "Healing the Epithelium: Solving the Problem from Two Sides," *J. Gastroenterol.*, 32: 122-126 (1997).

Powell, "Characterization of a Novel Messenger RNA and Immunochemical Detection of its Protein from Porcine Gastric Mucosa," *Ph.D. Dissertation*; The University of Chicago (1987).

Quaroni et al., "Epithelioid Cell Cultures From Rat Small Intestine," *J. Cell Biol.*, 80: 248-265 (1979).

Romanos et al., "Foreign Gene Expression in Yeast: a Review," *Yeast*, 8: 423-488 (1992).

Rotimi et al., "Acidity and Intestinal Bacteria: an In-Vitro Assessment of the Bactericidal Activity of Hydrochloric Acid on Intestinal Pathogens," *Afr. J. Medic. Med. Sci.*, 19: 275-280 (1990).

Sands et al., "The Trefoil Peptide Family," *Ann. Rev. Physiol.*, 58: 253-273 (1996).

Schlessinger et al., "Growth Factor Signaling by Receptor Tyrosine Kinases," *Neuron*, 9: 383-391 (1992).

Sears et al., "A Versatile Set of Vectors for Constituitive and Regulated Gene Expression in *Pichia pastoris*," Yeast, 14: 783-790 (1998).

Schmassmann et al., "Roles of Hepatocyte Growth Factor and Its Receptor Met During Gastric Ulcer Healing in Rats," *Gastroenterology*, 113, 1858-1872 (1997).

Segarini et al., "Membrane Binding Characteristics of Two Forms of Transforming Growth Factor-Beta," *J. Biol. Chem.*, 262 (30): 14655-14662 (1987).

Shiozaki et al., "Human stomach-specific gene, CA11, is down-regulated in gastric cancer," *International Journal of Oncology*, 4: 701-707 (2001).

Smith et al., "Single-Step Purification of Polypeptides Expressed in *Escherichia coli* as fusions with Glutathione S-transferase," *Gene*, 67: 31-40 (1988).

Tarnawski, "Cellular and Molecular Mechanisms of Ulcer Healing," *Drugs of Today*, 33 (10): 697-706 (1997).

Toback et al., "Induction of Growth in Kidney Epithelial Cells in Culture by Na+," *Proc. Nat. Acad. Sci.*, 77 (11): 6654-6656 (1980).

Waltz et al., "Functional Characterization of Domains Contained in Hepatocyte Growth Factor-Like Protein," *The Journal of Biological Chemistry*, 272:48 (1997).

Yarden et al., "Molecular Analysis of Signal Transduction by Growth Factors," *Biochemistry*, 27: 3113-3119 (1988).

Yoo et al., "Molecular Cloning and Nucleotide Sequence of Full-Length cDNA Coding for Porcine Gastrin," *PNAS*, 79: 1049-1053 (1982).

Yoshikawa et al., "Isolation of Two Novel Genes, Down-Regulated in Gastric Cancer," *Japanese Journal of Cancer Research, Japanese Cancer Association*, Tokyo, Japan 91:5, 456-463 (2000).

International Search Report issued in PCT/US2002/010148 (2003).

International Search Report issued in PCT/US2002/009885 (2004).

Search Report issued in EP 02728619 (2004).

Search Report issued in EP 02731209 (2005).

Search Report issued in EP 05010217 (2006).

Abitbol et al., "Hyperfractionated Radiation Therapy and 5-Fluorouracil, Cisplatin, and Mitomycin-C (± Granulocyte-Colony Stimulating Factor) in the Treatment of Patients with Locally Advanced Head and Neck Carcinoma," *Amer. Canc. Soc.*, 80(2): 266-276 (1997).

Arseneau et al., Discovering the cause of inflammatory bowl disease: lessons from animal models, *Current Opinion in Gastroenterology*, 16:310-317 (2000).

Clarkson et al., "Interventions for treating oral mucositis for patients with cancer receiving treatment (Review)," *The Cochrane Collaboration*, 1-53 (2008).

Dazzi et al., "Prophylaxis with GM-CSF mouthwashes does not reduce frequency and duration of severe oral mucositis in patients with solid tumors undergoing high-dose chemotherapy with autologous peripheral blood stem cell transplantation rescue: a double blind, randomized, placebo-controlled study," Annls of Oncology, 14:559-563(2003).

Farrell et al., "The effects of keratinocyte growth factor in preclinical models of mucositis," *Cell Prolif.*, 35 (Suppl. 1): 78-85 (2002).

Hibi et al., Animal models of inflammatory bowl disease, *Journal of Gastroenterology*, 37:409-417 (2002).

Hsueh et al, "Neonatl necrotizing enterocolitis: Clinical Considerations and Pathogenetic Concepts," *Pediatric and developmental Pathology*, 6: 6-23 (2002).

Israel et al., "Prevention of necrotizing enterocolitis in the rat with prenatal cortisone," *Gastroenterology*, 99(5): 1333-8 (1990).

Kannan et al., "Efficacy and Safety of Granulocyte Macrophage-Colony Stimulating Factor (GM-CSF) on the Frequency and Severity of Radiation Mucositis in Patients with Head and neck Carcinoma," *Int. J. Radiation Onc. Biol. Phys.*, 37(5): 1005-1010 (1997).

Ovalle et al. "Upper Digestive System," *Netter's Essential Histology, Elsevier Health Sciences*, Philadelphia, PA, p. 264-267 and 304-305 (2007).

Ramsay et al., "Colony-Stimulating Factor-1 Promotes Clonogenic Growth of Normal Murine Colonic Crypt Epithelial Cells In Vitro," *J. Interferon & Cytok. Res.*, 24: 416-427 (2004).

Scully et al., "Oral Mucositis," *Oral Diseases*, 12: 229-241 (2006).

Spielberger et al., "Palifermin for Oral Mucositis after Intensive Therapy for Hematologic Cancers," New England J. Med., 351(25): 2590-2598 (2004).

Tejedor et al., "Hyperfractionated radiotherapy concomitant with cisplatin and granulocyte colony-stimulating factor (filgrastim) for laryngeal carcinoma," *Cytokines, Cell. & Mol. Ther.*, 6: 35-39 (2000).

Valcárcel et al., "Mouth-washings with recombinant human granulocyte—macrophage colony stimulating factor (rhGM-CSF) do not improve grade III-IV oropharyngeal mucositis (OM) in patients with hematological malignancies undergoing stem cell transplantation. Results of a randomized double-blind placebo-controlled study," Bone Marrow Transpl., 29: 783-787 (2002.).

* cited by examiner

Close to 400,000 Patients Per Year Suffer From Mucositis During Cancer Therapy Stem cell transplant and radiation +/ - chemotherapy for solid tumor (head and neck cancer, non –small cell lung cancer) patients have the highest risk for severe mucositis – Mild, moderate, and severe mucositis can have serious clinical a nd economic consequences Source: Mattson Jack Database 2003; NCI; Note: 400,000 patients in the US; CRC = colorectal cancer; NHL = non-Hodgkin's lymphoma

FIG. 7

METHODS AND COMPOSITIONS TO TREAT MUCOSITIS

CROSS-REFERENCE TO RELATED PATENT APPLICATIONS

This patent application is a U.S. Nationalization of international patent application no. PCT/US2006/018014, filed May 9, 2006, which claims priority to European Application No. 05010217.7, filed May 10, 2005, and U.S. Provisional Patent Application No. 60/790,177, filed Apr. 7, 2006.

BACKGROUND

Antrum Mucosal Protein (AMP)-18 (also called gastrokine-1) is an 18 kDa protein expressed in mucosal epithelial cells of the gastric antrum. Within stomach cells the protein is found in vesicles together with mucins just under the lumenal cell surface. AMP-18 is secreted onto the stomach lining as a component of the viscoelastic gel that coats the mucosal surface. The native protein and a 21-mer peptide comprising amino acids 77-97 (AMP77-97 peptide) both function as mitogens and motogens for gastrointestinal (GI) epithelial cells. AMP77-97 peptide also acts on the tight junctions (TJs) (FIG. 1) that hold GI mucosal epithelial cells together by preventing the loss of specific proteins such as occludin and ZO-1 after injury, and by facilitating assembly of TJ proteins to repair mucosal barrier function and structure which could protect the gut against the entry of bacteria, their toxins, and other potentially injurious molecules that reside in the gut lumen.

Mucositis is an inflammatory and ulcerative injury of the mouth, throat or GI tract most commonly caused by chemo- or radiation therapy for cancer. This disease has its onset when chemotherapy or radiation disrupts the mucosal surface of the mouth and other portions of the GI tract, affecting both the epithelial layer and the underlying connective tissue. In severe cases, oral mucositis can be extremely painful, preventing the patient from eating, and requiring hospitalization for hydration, narcotics for pain, and/or total parenteral nutrition. Pain resulting from mucositis is so severe that it is often cited by cancer patients as the primary reason for discontinuing treatment. Patients suffering from mucositis may feel as if they were drinking scalding hot water and scraping the inside of their mouth with coarse sand paper followed by running their tongue over a cheese grater. Mucositis can also be life-threatening because oral ulcerations can permit the entry of bacteria into the bloodstream, a situation which can be fatal in a patient already immune-compromised by treatment for cancer.

Figure 7:
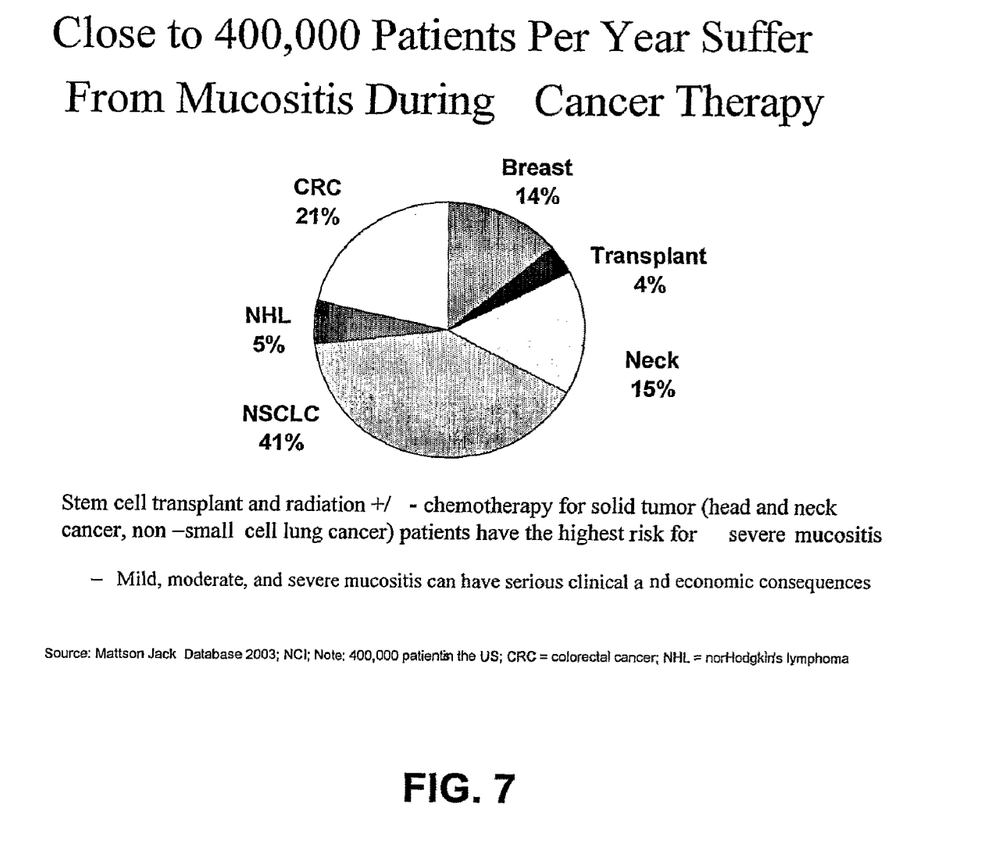
FIG. 7 shows causes of mucositis during cancer therapy. CRC=colorectal cancer; NHL=non-Hodgkins lymphoma; NSCLC=non-small-cell lung cancer.

Overall, mucositis affects 15-40 percent of patients receiving standard-dose chemotherapy and 76-100 percent of patients receiving higher doses of chemotherapy for bone marrow transplantation (FIG. 7). Mucositis also affects virtually all patients receiving radiation therapy for head and neck cancer, as well as patients receiving radiation along the GI tract. For example, esophagitis (or esophageal mucositis) is a major complication of chemoradiation therapy in patients with non-small cell lung cancer that produces significant morbidity and results in treatment interruptions. Mucositis afflicts over 400,000 patients a year in the US, and the incidence is growing as the need for radiation and chemotherapy treatments grows. This represents a potential annual market of greater than $800 million in the US.

Treatment of oral mucositis is a significant unmet medical need. Current treatment strategies are primarily palliative and include mucosal coating mixtures that may contain topical anesthetics and antibiotics to prevent infection. These treatments provide little benefit, and do not speed healing or decrease severity of mucositis. The only currently approved therapeutic for mucositis is Kepivance™ which is the known mitogenic protein keratinocyte growth factor (KGF) that must be administered intravenously. Kepivance™ is approved for a single indication which comprises only 4% of the total mucositis population, i.e., treatment of mucositis resulting from pre-conditioning regimens (chemotherapy and radiation) in stem-cell transplant patients.

SUMMARY OF THE DISCLOSURE

The present disclosure and the priority application, for the first time, enablingly demonstrate that peptide compositions derived from AMP-18 protein surprisingly reduce mucositis in mammals. In addition, peptide compositions, including dosage and administration modes, enablingly demonstrate that AMP-18 protein derived peptides reduce the intensity of mucositis and/or delays the onset of mucositis. Thus, the disclosures in the present application and the priority application, expressly demonstrate that specific peptides derived from a gastrokine, e.g., AMP-18, are therapeutically effective to treat, reduce the intensity, delay the onset, and minimize the duration of mucositis in mammals.

AMP-18 protein and its derived peptides act as mitogens and motogens. AMP-18 protein includes purified protein and recombinant protein. AMP-18-derived peptides includes AMP-18-derived peptides from human, mice, and pig. In addition to AMP77-97 peptide, other suitable human AMP-derived peptides include AMP58-99 (KKTCIVHK-MKKEVMPSIQSLDALVKEKKLQGKGPGGPPPKGL) (SEQ ID NO: 1), AMP84-97 (KKLQGKGPGGPPPK) (SEQ ID NO: 2), AMP84-101 (KKLQGKGPGGPPPKGLMY) (SEQ ID NO: 3), AMP77-101 (LDALVKEKKLQGKGPG-GPPPKGLMY) (SEQ ID NO: 4), and mouse AMP-derived peptide77-99 (LDTMVKEQKGKGPGGAPPKDLMY) (SEQ ID NO: 5). The amino acid positions, e.g., 77-97, refer to the amino acid positions of the mature/processed form of AMP-18 protein from human or from mouse or pig as indicated.

AMP77-97 peptide's effects include mitogenic and motogenic functions. The AMP77-97 peptide stimulates healing of injured mucosal surfaces by its actions to facilitate restitution and cell proliferation after injury, and enhance formation of new tight junctions between cells to repair the mucosal barrier. AMP77-97 peptide provides a useful treatment of diseases and abnormal conditions of the GI tract, including oral mucositis which continues to be a significant unmet medical need. AMP77-97 peptide is effective in alleviating mucositis, for example cancer-therapy induced mucositis. For example, AMP 77-99 peptide derived from murine AMP-18 protein is also suitable to treat mucositis.

Figure 2:
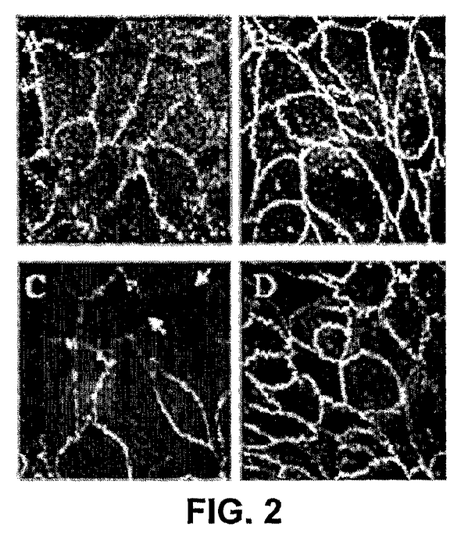
Figure 3:
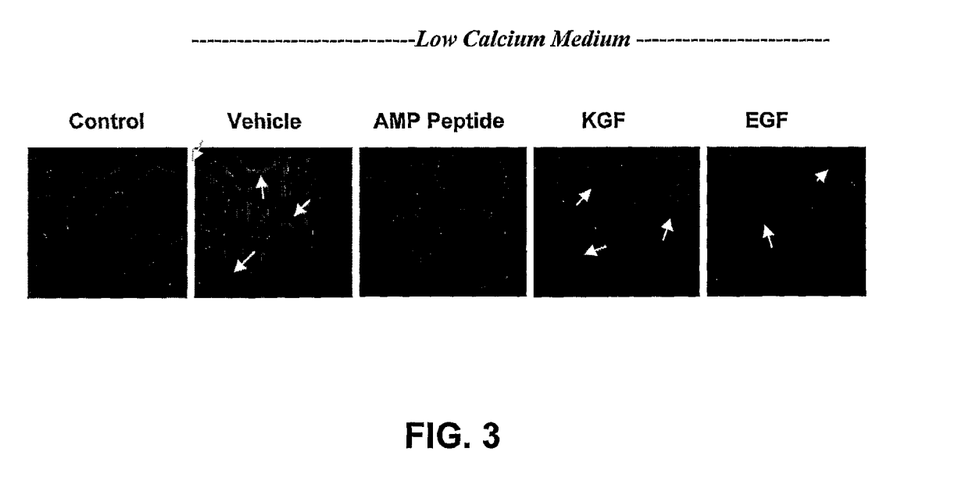

The AMP77-97 peptide prevented decreases in TJ proteins and epithelial integrity seen after treatment of human colonic Caco2 (C2) cell monolayers with the oxidant monochloramine, which disrupts intercellular junctions (FIG. 2; C,D). These cells were exposed to low-calcium medium (3 μM) for 1 hr to disrupt TJs, and then allowed to recover in medium containing AMP77-97 peptide, epidermal growth factor (EGF) or keratinocyte growth factor (KGF-1) which are known epithelial cell mitogens that might facilitate recovery of disrupted TJs. The results in FIG. 3 show that only treatment with AMP77-97 peptide facilitated rapid recovery of TJs between the cells. Thus, AMP77-97 peptide displays an effect on these epithelial cell TJs not seen with either EGF or KGF. At the molecular level, AMP77-97 peptide facilitates the formation of TJs by enhancing translocation of several proteins (protein kinase C-zeta, Par6, Cdc42, ECT2 and Par3) from the cytosol into TJ domains.

Possible toxic effects of AMP77-97 peptide on the hERG-related potassium current as tested in a high throughput assay (IonWorks™ HT System, Essen Instruments, Ann Arbor, Mich.; MPICardIon, Mattawan, Mich.), using the human hERG channel cloned into Chinese Hamster Lung (CHL) cells were investigated. There were no effects on the current at concentrations up to 33 µM indicating that the peptide is not a cell toxin.

When administered subcutaneously to mice, AMP77-97 peptide increased TJ protein components in intestinal, but not kidney or liver tissue. Thus, AMP77-97 peptide, in addition to promoting the repair of mucosal surfaces via cell growth and migration, protects existing TJs in GI epithelial cells and thereby preserves mucosal barrier function and structure. Treatment of C2 cells in culture with AMP77-97 peptide has also been shown to preserve transepithelial electrical resistance, a measure of barrier function which is a marker for mucosal integrity of the GI tract. This effect was accompanied by stabilization of perijunctional actin molecules via the p38 MAP kinase/hsp27/actin pathway, a signal-transduction pathway that is activated by AMP77-97 peptide.

Pharmaceutical compositions including AMP-18 protein and peptides derived from AMP-18 protein are suitable to treat mucositis.

A pharmaceutical composition includes a therapeutically effective amount of a peptide derived from AMP-18 and a pharmaceutically acceptable carrier, wherein the peptide is effective in treating mucositis. A therapeutically effective amount corresponds to about 1-100 mg/kg of body weight.

The pharmaceutical composition includes a peptide that has an amino acid sequence selected from LDALVKEKKLQGKGPGGPPPK (SEQ ID NO: 6) (AMP77-97), KKTCIVHKMKKEVMP-SIQSLDALVKEKKLQGKGPGGPPPKGL (SEQ ID NO:1) (AMP58-99), KKLQGKGPGGPPPK (SEQ ID NO: 2) (AMP84-97), KKLQGKGPGGPPPKGLMY (SEQ ID NO: 3) (AMP84-101), LDALVKEKKLQGKGPGGPPPKGLMY (SEQ ID NO: 4) (AMP77-101), and mouse AMP-derived peptide LDTMVKEQKGKGPGGAPPKDLMY (SEQ ID NO: 5) (AMP77-99).

The mucositis includes oral mucositis. Mucositis is induced by a therapy to treat cancer that includes radiation therapy, chemo therapy or a combination of chemo and radiation therapies.

The pharmaceutical composition can be administered parenterally. Suitable modes of administration includes oral administration, intravenous administration, subcutaneous administration, topical administration, transdermal administration, intraperitoneal administration, transmucosal administration and nasal administration.

A method to reduce or delay the onset of mucositis includes the steps of:
(a) administering a pharmaceutical composition comprising a therapeutically effective amount of a peptide derived from AMP-18 and a pharmaceutically acceptable carrier; and
(b) determining that the peptide derived from AMP-18 delays the onset, or reduces the intensity or duration of mucositis or a combination thereof.

A method to alleviate cancer-therapy induced mucositis, includes:
(a) obtaining peptide AMP77-97 or peptides derived from AMP-18 protein; and
(b) administering the peptide or protein to a subject in need thereof.

A method to repair injuries to the gastric mucosa, includes:
(a) obtaining peptide AMP77-97 peptide or peptides derived from AMP-18 protein; and
(b) administering the peptide or protein to a subject in need thereof.

In addition, a modified peptide may be produced by the following method:
(a) eliminating major protease sites in an unmodified peptide amino acid sequence by amino acid substitution or deletion; and/or
(b) introducing into the modified peptide, amino acid analogs of amino acids in the unmodified peptide.

A pharmaceutical composition includes at least one growth stimulating peptide and a pharmaceutically acceptable carrier.

A method to stimulate growth of epithelial cells in the gastrointestinal tract of mammals includes:
(a) contacting the epithelial cells with a composition of AMP-18 protein or a peptide derived from a protein of the group; and
(b) providing environmental conditions suitable for cellular growth stimulating activity of the protein.

A method to stimulate migration of epithelial cells after injury to the gastrointestinal tract of mammals includes:
(a) contacting the epithelial cells with a composition comprising a peptide derived from the protein; and
(b) providing environmental conditions allowing migration of the epithelial cells.

A method for cell protection of damaged epithelial cells and the tight junctions between them in the gastrointestinal tract of mammals includes:
(a) contacting the damaged epithelial cells with a composition including a protein of the AMP-18 group or a peptide derived from the protein; and
(b) providing environmental conditions allowing repair of the epithelial cells and their tight junctions.

The damaged cells may form an ulcer.

A method to prevent or reduce in a subject in need thereof recurrences of gastric and duodenal infections, inflammation and ulceration caused by *H. pylori*, includes the steps of:
(a) obtaining peptide AMP77-97 or AMP-18 protein; and
(b) administering the peptide or protein to subject in need thereof with mucositis in the mouth and/or elsewhere in the GI tract; or with inflammatory bowel disease, gastric or duodenal ulcers, and other diseases that disrupt GI mucosal barrier structure and function.

The term "agent" as used herein includes nucleic acids, proteins, protein fragments, peptides, synthetic peptides, peptidomimetics, analogs thereof, small molecules, inhibitors, and any chemical, organic or bioorganic molecule capable of affecting protein-protein interaction or a cellular process.

The term "AMP-18 derived peptides" means peptides, modified peptide sequences with amino acid substitutions or amino acid analogs or amino acid deletions compared to a corresponding region in AMP-18, and peptidomimetics that correspond to a particular region in AMP-18 protein. The AMP 18-derived peptides can range from about 5-50 amino acids in length or about 5-20 amino acids in length or about 5-10 amino acids in length. The AMP-18-derived peptides can also be modified to affect their lipophilicity to enhance peptide delivery to mucosal epithelial cells of the mouth and GI tract. The peptides can be synthesized ("synthetic peptides") or can also be produced through recombinant techniques ("recombinant peptide"). These peptides can also be engineered to increase their in vivo stability without significantly affecting their efficacy to promote cell growth and migration, enhance formation and assembly of tight junction proteins, and mediate cell protection.

A "peptide derivative" is used to mean a molecule having an amino acid sequence of a region of AMP-18 protein or of an AMP-18 protein homolog, but additionally having at least one chemical modification of one or more of its amino acid side groups, α-carbon atoms, terminal amino group, or terminal carboxylic acid group. A chemical modification includes adding chemical moieties, creating new bonds, and removing chemical moieties. Modifications at amino acid side groups include acylation of lysine, ε-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a C1-C4 alkyl. Furthermore, one or more side groups, or terminal groups, may be protected by protective groups known to the ordinarily-skilled protein chemist. The α-carbon of an amino acid may be mono- or di-methylated.

BRIEF DESCRIPTION OF THE DRAWINGS

FIG. 2 shows the effects of AMP77-97 peptide on occludin visualized by confocal microscopy in C2 cells under control conditions and following oxidant injury. Occludin immunoreactivity in a control cell monolayer (panel A) formed a uniform band outlining the cell junctions that was more intense than in the cytoplasm. When cells were exposed to AMP77-97 peptide for 18 hr (panel B), occludin appeared to be relatively more abundant in the TJs and less in the cytoplasm than in control cells. Following exposure to the oxidant monochloramine (0.3 mM) for 30 min (panel C), occludin intensity at the cell junctions was reduced and at some sites was discontinuous; occasionally it was barely visible (arrows). In cells that were pretreated with AMP77-97 peptide prior to the oxidant (panel D), occludin immunoreactivity at the cell junctions was more intense than in untreated injured cells.

FIG. 3 shows that AMP77-97 peptide, but not epidermal growth (EGF) or keratinocyte growth factor (KGF) facilitates formation of new tight junctions in human colonic epithelial cells after their disruption by exposure to low-calcium medium. Localization of the tight junction protein ZO-1 was monitored by indirect immunofluorescence laser scanning confocal microscopy in confluent monolayers of C2 cells. Cultures in control medium (calcium=1.8 mM) exhibit intact tight junctions. To disrupt tight junctions, cells were switched to low-calcium medium (3 μM) for 1 hour. Then a growth factor at a known mitogenic concentration was added to the medium, and 2 hours later its effect on tight junction formation was assessed by confocal microscopy. Vehicle, AMP peptide (8 μg/ml), KGF-1 (100 ng/ml), and EGF (100 ng/ml) were compared. Arrows indicate persistent separation of cells with TJ disruption and apparent loss of ZO-1 in cultures exposed to vehicle, KGF-1, or EGF. In contrast, AMP peptide facilitated recovery of ZO-1 and the formation of intact tight junctions.

In FIG. 5A, the pouch is completely healthy with no erythema or vasodilation. FIG. 5B illustrates light to severe erythema and vasodilation with no erosion of the mucosa. FIG. 5C illustrates severe erythema and vasodilation with erosion and decreased stippling of superficial mucosa leaving denuded areas. FIG. 5D illustrates the formation of an ulcer occupying ¼ or less of the pouch. FIG. 5E illustrates the total size of the ulcer occupying ½ of the pouch with loss of pliability. In FIG. 5F, ulceration to virtually all of the pouch can only be partially averted.

DETAILED DESCRIPTION OF THE DISCLOSURE

Peptide compositions derived from AMP-18 protein surprisingly reduce mucositis in mammals. The present disclosure and the priority application, for the first time, provide data to enablingly demonstrate that specific peptides derived from a gastrokine, e.g., AMP-18, are therapeutically effective to treat, reduce the intensity, delay the onset, and minimize the duration of mucositis in mammals. In addition, peptide compositions, including dosage and administration modes, enablingly demonstrate that AMP-18 protein derived peptides reduce the intensity of mucositis and/or delays the onset of mucositis.

Figure 1:
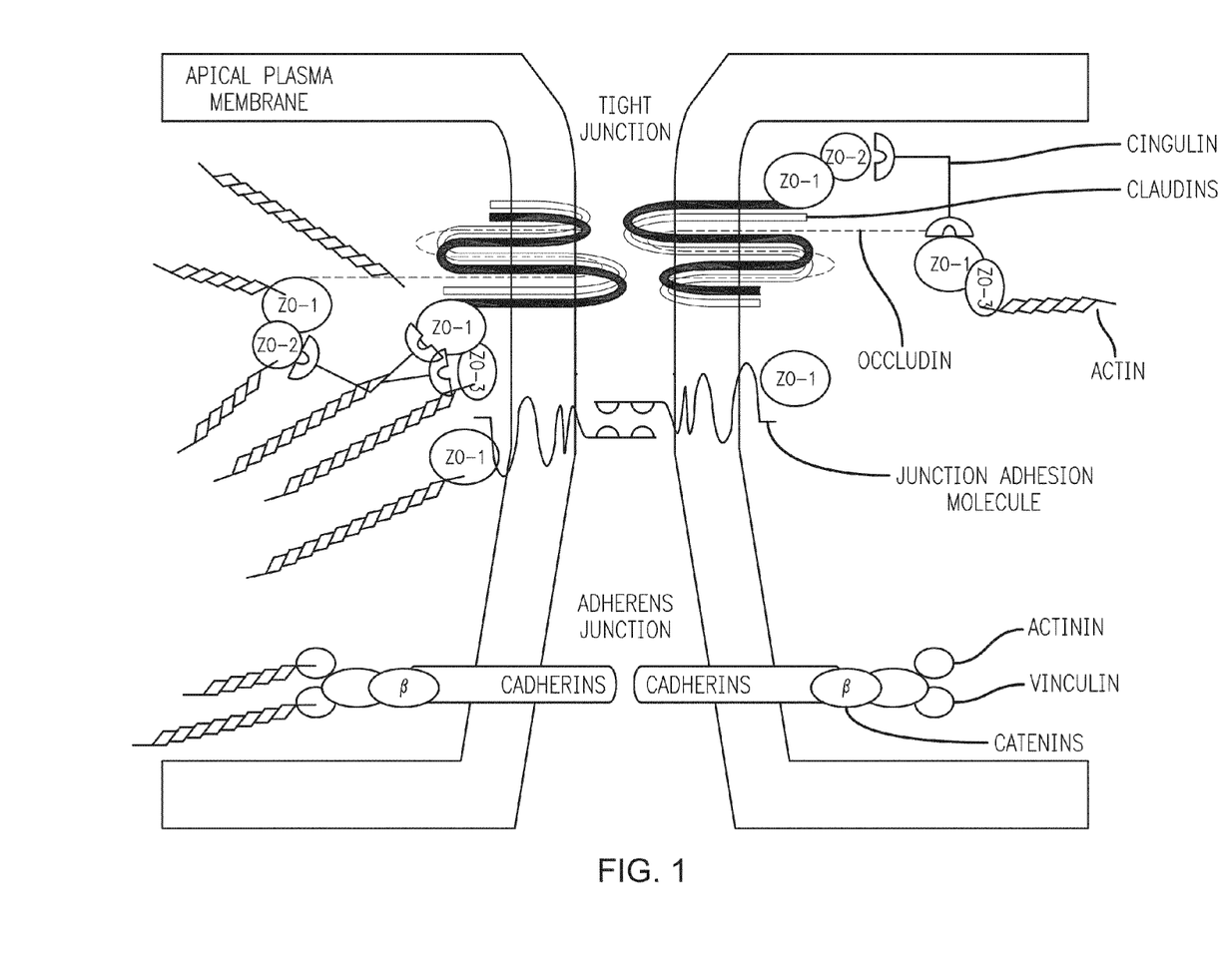
FIG. 1 is a schematic illustration of tight junctions and their associated proteins.

AMP77-97 peptide acts in cell culture as a mitogen and a motogen, and appears to protect against injury to tight junctions between mucosal epithelial cells (FIG. 1). AMP77-97 peptide is a therapeutic agent in oral mucositis. In two different models of radiation-induced injury to oral epithelia in mouse and hamster, administration of AMP77-97 peptide reduced the duration and extent of ulcerative lesions on the tongue and buccal mucosa thereby significantly accelerating recovery.

Because of its protective and healing effects on the GI epithelium, AMP77-97 peptide is useful in treating a wide range of diseases of the GI tract such as esophagitis, peptic ulcer disease, and inflammatory bowel disease (ulcerative colitis, Crohn's disease) (IBD). In IBD, inflammatory reactions compromise barrier functions such as vectorial transport of nutrients, water and electrolytes, and allow bacterial toxins and pro-inflammatory molecules to pass from the gut lumen into the intestinal submucosa, causing considerable morbidity and mortality (patient population ~1 million in the US). Current therapies for these latter diseases include steroids and other anti-inflammatory agents which target unknown immune causes of disease. No therapy aimed at repair of the intestinal epithelium is currently available, so AMP77-97 peptide has the potential to be a therapy for preventing injury or speeding recovery from multiple types of GI insults as evidenced by AMP77-97 peptide delaying appearance of blood in the stool and reducing weight loss in mice in which acute colitis was induced by dextran sulfate sodium.

FIG. 2 shows the effects of AMP77-97 peptide on occludin as visualized by confocal microscopy in C2 cells under control conditions and following oxidant injury. Occludin immunoreactivity in a control cell monolayer (panel A) formed a uniform band outlining the cell junctions that was more intense than in the cytoplasm. When cells were exposed to AMP77-97 peptide for 18 hrs (panel B), occludin appeared to be relatively more abundant in the TJs and less in the cytoplasm than in control cells. Following exposure to the oxidant monochloramine (0.3 mM) for 30 min (panel C), occludin intensity at the cell junctions was reduced and at some sites was discontinuous; occasionally it was barely visible (arrows). In cells that were pretreated with AMP77-97 peptide prior to the oxidant (panel D), occludin immunoreactivity at the cell junctions was more intense than in untreated injured cells. The observations demonstrate that AMP77-97 peptide can protect the tight junction protein occludin against oxidant injury in human colonic epithelial cells. Similar results were also obtained for the tight junction protein ZO-1.

Other AMP-18 derived peptides such as, for example, KKTCIVHKMKKEVMP-SIQSLDALVKEKKLQGKGPGGPPPKGL (SEQ ID NO: 1) (AMP58-99), KKLQGKGPGGPPPK (SEQ ID NO: 2) (AMP84-97), KKLQGKGPGGPPPKGLMY (SEQ ID NO: 3) (AMP84-101), LDALVKEKKLQGKGPGGPPPKGLMY (SEQ ID NO: 4) (AMP77-101), and mouse AMP-derived peptide LDTMVKEQKGKGPGGAPPKDLMY (SEQ ID NO: 5) (AMP77-99) also suitable for use in treating mucositis based on their mitogenic and motogenic functions. Effects of these peptides can be tested using the mouse biomodels disclosed herein.

Derivatives and analogs of AMP-18 peptides may be full length or other than full length, if the derivative or analog contains a modified nucleic acid or amino acid, as described herein. Derivatives or analogs of the nucleic acids or proteins of the invention include, molecules comprising regions that are substantially homologous to the nucleic acids or proteins of the invention, in various embodiments, by at least about 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel et al., (1993).

Peptides and other compositions disclosed herein can be administered via any suitable means. For example, the peptide compositions may be diluted in saline or any suitable buffer and administered directly intravenously, subcutaneously, topically, and/or intraperitoneally.

Administration of the compositions disclosed herein may be via any route known to be effective by the physician of ordinary skill. Peripheral, parenteral administrations, and topical administrations are suitable. Dosage of the AMP-18-derived peptides depends on the efficacy of the peptide, stability of the peptide in vivo, mode of administration, body weight, age of the patient and other factors that are commonly considered by a skilled artisan. For example, dosage of a AMP-18-derived peptide drug can range from about 0.1-10.0 mg/kg body weight or from about 10-20 mg/kg body weight or from about 0.5-50 mg/kg body weight or from about 10.0-70.0 mg/kg body weight. Parenteral administration is commonly understood in the medical literature as the injection of a dosage form into the body by a sterile syringe. Peripheral parenteral routes include intravenous, intramuscular, subcutaneous, and intraperitoneal routes of administration. Intravenous, intramuscular, and subcutaneous routes of administration of the compositions disclosed herein are suitable. For parenteral administration, the peptides disclosed herein can be combined with phosphate buffered saline (PBS) or any suitable pyrogen-free pharmaceutical grade buffer that meets FDA standard for human subject administration. As used herein, "pharmaceutically acceptable carrier" includes any and all solvents, diluents, or other liquid vehicle, dispersion or suspension aids, surface active agents, isotonic agents, thickening or emulsifying agents, preservatives and the like, as suited to the particular dosage form desired. Remington (2000) discloses various carriers used in formulating pharmaceutical compositions and known techniques for the preparation thereof. Solutions or suspensions of the compositions described herein can also include a sterile diluent, such as water for injection, saline solution, fixed oils, polyethylene glycols, glycerine, propyleneglycol or other synthetic solvents; chelating agents, such as EDTA; buffers, such as acetates, citrates or phosphates; and agents for the adjustment of tonicity, such as sodium chloride or dextrose. A parenteral preparation of the compositions can be enclosed in ampoules, disposable syringes or multiple dose vials made of glass or plastic, in accordance with standard practice in the field. The compositions disclosed herein can be stored as a lyophilized sterile powder in vials prior to reconstitution and the unreconstituted product may be stored at −20° C.

Example 1

Effect of AMP77-97 Peptide in Mouse Model of Mucositis

The capacity of the AMP77-97 peptide to induce epithelial thickening of oral mucosal surfaces in mice and hamsters was studied to determine if these animals could be used to evaluate the potential of AMP77-97 peptide in the treatment of oral mucositis. In Study 1, female BDF-1 mice (n=8) and Syrian golden hamsters (n=8) were given daily subcutaneous injections of saline, mouse AMP77-97 peptide at 5 mg/kg, or 25 mg/kg for five days. The results of histological studies revealed that there was significant epithelial hyperplasia on the dorsal surface of the tongues in the BDF-1 mice treated with AMP77-97 peptide, and that in many animals hyperplasia was accompanied by hyperkeratosis. There also appeared to be an increase in both hyperplasia and hyperkeratosis with increasing dose (more prevalent/pronounced in the animals receiving 25 mg/kg than those receiving 5 mg/kg) and duration of dosing (there were some effects seen at 2 days, but were more readily seen after 5 consecutive days). The effect was more easily observed on the dorsal than the ventral surface of the tongue. An increase in the degree of keratinization in the esophagus was also observed that increased with increasing dose of AMP77-97 peptide, and with an increase in the number of doses. The effects of AMP77-97 peptide were also evident in the hamster tongue, but less pronounced, with hyperplasia being much more commonly observed than hyperkeratosis. Based on the analysis of weight gain and the lack of mortality during the study, there was no evidence of any toxicity associated with treatment with AMP77-97 peptide in either mice or hamsters. In summary, treatment with AMP77-97 peptide caused thickening in the oral epithelium in both BDF-1 mice and Syrian Golden hamsters suggesting that it would be effective in the treatment of oral mucositis in both animal models.

In Study 2, the effect of AMP77-97 peptide on thickening in the oral epithelium was compared in five different strains of mice. The results showed that the BDF-1 mice (n=4) exhibited the most pronounced and universally seen increase in hyperplasia on both dorsal and ventral surfaces of the tongue. However, treatment with AMP77-97 peptide also caused thickening of the oral epithelium in each of the following mouse strains evaluated: C3H/OuJ, C3H/HeN, C57Bl/6, and Balb c. Hyperkeratosis was again observed in the esophagus of BDF-1 mice, and was also seen in C3H/HeN mice. There was no evidence of any toxicity associated with treatment of AMP77-97 peptide in any of the five mouse strains, based on analysis of weight gain and lack of mortality.

Figure 4:
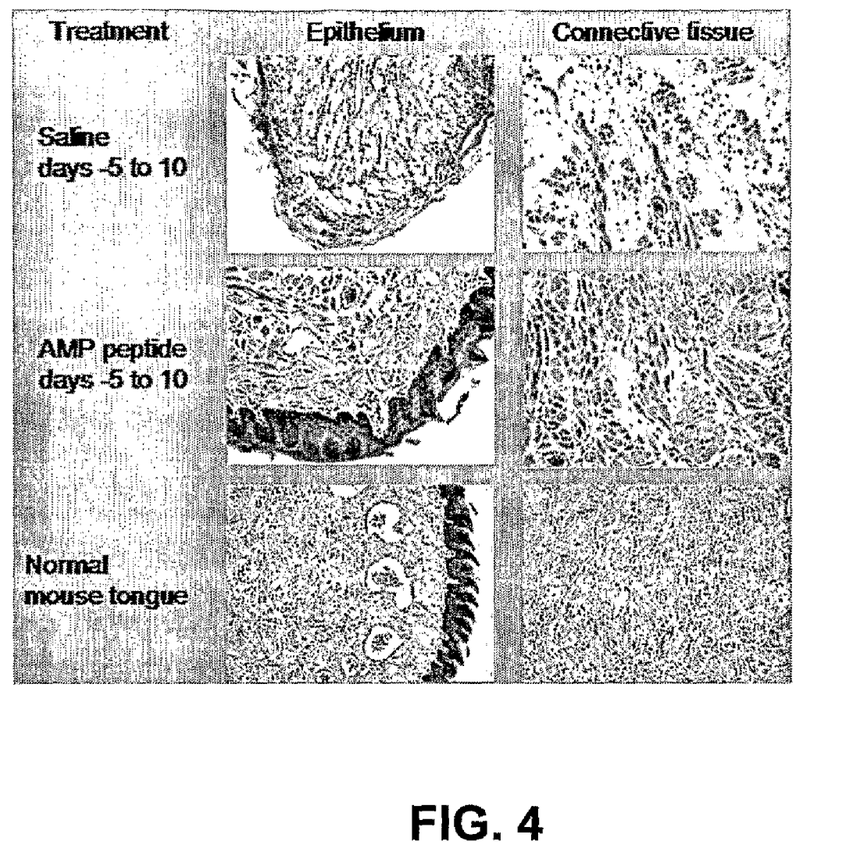
FIG. 4 shows the effects of AMP77-97 peptide on radiation-induced tongue damage in the mouse. AMP77-97 peptide (25 mg/kg, s.c.) was administered 5 days before and 10 days after radiation of the tongue in the BDF-1 mouse model of oral mucositis. Photomicrographs were prepared 10 days after radiation. Tissue from control irradiated mice treated with vehicle (saline) show substantial epithelial and connective tissue cell loss in both compartments compared to normal mouse tongue. In contrast, tissue from animals treated with AMP77-97 peptide exhibits a thickened hyperkeratotic epithelial surface and a largely intact connective tissue compartment.

In Study 3, mucositis was induced in BDF-1 mice (n=40) by administering a single dose of radiation of 30 Gy to the snout. To evaluate the effect of AMP77-97 peptide in this setting of radiation-induced injury of the epithelial and connective tissue compartments of the tongue, mouse AMP77-97 peptide (25 mg/kg) was administered once daily subcutaneously before and after radiation (days −5 to 10; radiation on day 0). Histological analysis of the tongue revealed that administration of AMP77-97 peptide reduced signs of mucositis in both the epithelial cell layer (FIG. 4, dark layer in slides under "Epithelium") and in connective tissue, relative to saline-treated controls (FIG. 4, note cellularity of "Connective tissue"). The evaluation was performed on day 10 when mucositis injury is at its peak. This effect on connective tissue supported that AMP77-97 peptide has beneficial effects on multiple cell and tissue types damaged by radiation. There was no evidence of any toxicity associated with AMP77-97 peptide treatment.

Example 2

Effect of AMP77-97 Peptide in Hamster Model of Mucositis

Figure 5:
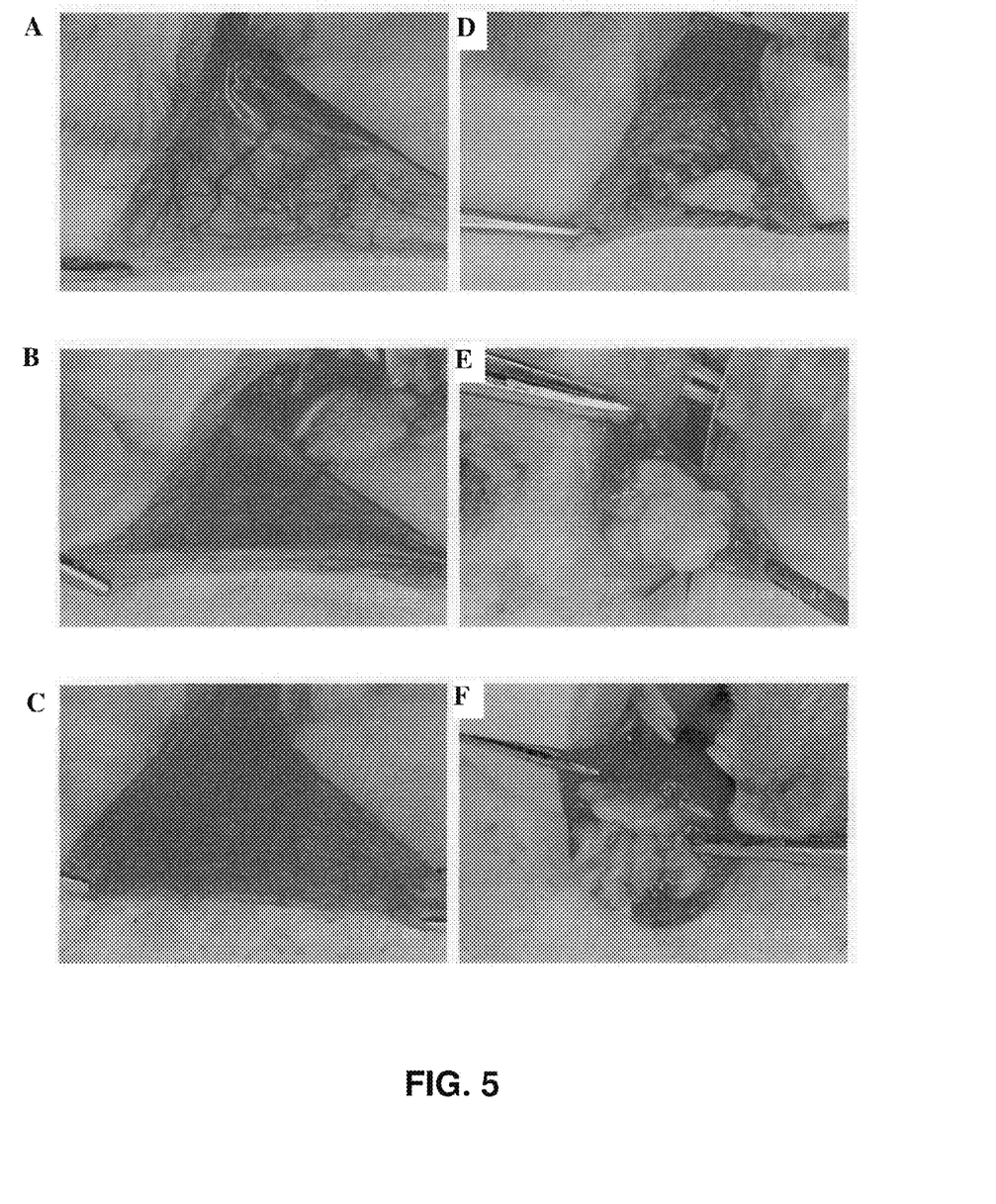
FIG. 5 shows scoring system for mucositis in the hamster cheek pouch.

AMP77-97 peptide was tested in a hamster mucositis model in which radiation is used to injure the mucosal surface of the cheek pouch. In Study 4, male Syrian Golden hamsters (n=32) were given an acute radiation dose of 40 Gy directed to the mucosal surface of the everted left buccal cheek pouch. This results in peak injury 14-16 days later with clinically significant mucositis observed on days 12 through 28. AMP77-97 peptide (0-40 mg/kg) was administered by subcutaneous injection once daily starting five days before radiation (day −5) and continued until day 15, excluding day of radiation (day 0). Scoring in this model uses the same objective assessments of damage as the World Health Organization (WHO) scoring system used clinically. Every other day starting on day 6, photographs of pouches were taken and evaluated using the criteria depicted in FIG. 5. These photographs were scored by observers blinded to the experimental protocol. Briefly, a score of 1-2 represents a mild stage of the disease (erythema, vasodilation, erosion of superficial aspects of mucosa), whereas a score of 3-5 indicates moderate to severe mucositis (ulcers with cumulative size from ¼ to virtually all of the pouch).

Figure 6:
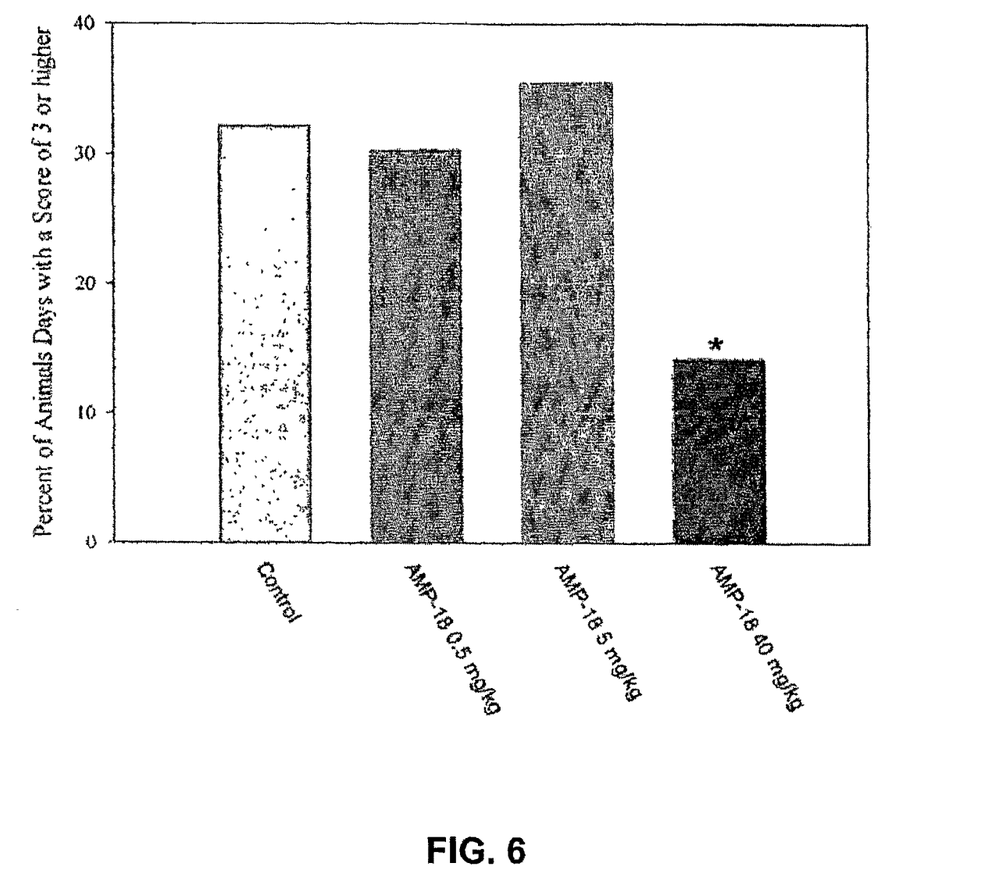
FIG. 6 shows the effects of AMP77-97 peptide on the number of animal days with mucositis scores of 3 or greater. The level of clinically significant mucositis was defined by presentation with open ulcers on the buccal mucosa after radiation (a score of 3 or greater). The total number of days in which a hamster exhibited an elevated score was summed and expressed as a percentage of the total number of days scored. The asterisk denotes that treatment with AMP-18 peptide (40 mg/kg) resulted in a statistically significant lower mucositis score when compared to the vehicle (PBS) using a Chi-squared test (P<0.001).

In the control group in which phosphate-buffered saline (PBS; vehicle) was given, peak levels of mucositis were seen on day 16 when the mean score reached 3.1 (severe erythema and vasodilation; cumulative size of one or more ulcers equals ¼ of the pouch). In the group receiving AMP77-97 peptide (40 mg/kg), the peak of mucositis did not occur until day 18, when the mean score was reduced to 2.6. The AMP77-97 peptide-treated hamsters then recovered more quickly than the control group, reaching a score of 1.1 by day 26. Additional analysis revealed that peptide-treated animals showed a significant reduction in the number of days with a mucositis score of 3 or higher (mucosal ulceration) compared to vehicle-treated animals (P<0.001), thereby providing strong evidence of a protective effect. Hamsters treated with the vehicle (PBS) in the control group had a score of 3 or higher on 32.1% of the animal days evaluated, whereas the group treated with AMP77-97 peptide had a significant reduction with only 14.1% of animal days in this group having a score of 3 or higher (P<0.001) (FIG. 6). Animals treated with AMP77-97 peptide also showed a statistically significant reduction in mucositis scores on day 14 (P=0.022), day 20 (P=0.042) and day 26 (P=0.032). In this model of mucositis, statistically significant improvement on two or more days is regarded as a clinically meaningful benefit indicating that treatment with AMP77-97 peptide resulted in an improved outcome during the course of oral mucositis.

Similar results were obtained when Study 5 was performed. Hamsters treated with AMP77-97 peptide at 40 mg/kg on days −5 to −1 and days 1 to 15 showed a statistically significant reduction in the number of days with a mucositis score of 3 or higher (P=0.018), and significant reductions on day 26 (P=0.036) and on day 28 (P=0.020).

In a separate test of efficacy (Study 6), AMP77-97 peptide was administered topically into the hamster cheek pouch (n=32). Doses of 0.5, 5 or 50 mg/kg AMP77-97 peptide in PBS were placed in the pouch three times daily from days −5 to −1 before radiation and 1 to 15 after radiation. Results presented in Table 1 show that AMP77-97 peptide can significantly decrease mucositis in this model of mucositis when administered topically, and that the effect is also dose dependent. In each of the studies using the hamster cheek pouch as well as the mouse model of mucositis, there were no signs of toxicity as measured by weight loss or mortality.

TABLE 1

Animals with a mucositis score of 3 or higher when AMP77-97 peptide was given topically

| Group | Days >=3 | Days <3 | Total Days | Chi square vs. control | P value |
| --- | --- | --- | --- | --- | --- |
| Control | 88 | 104 | 192 | | |
| AMP peptide 0.5 mg/kg | 76 | 116 | 192 | 1.2880 | 0.256 |
| AMP peptide 5 mg/kg | 68 | 125 | 192 | 3.8970 | 0.048 |
| AMP peptide 50 mg/kg | 62 | 130 | 192 | 6.8380 | 0.009 |

Example 3

Therapeutic Efficacy

The data disclosed herein points to multiple therapeutic targets for AMP-18/AMP peptide. These include treatment of IBD by: (a) preventing or decreasing the frequency and intensity of acute exacerbations of this episodic disease by the AMP77-97 peptide's cell protective effect, and (b) speeding recovery of the colonic mucosal epithelium after an attack of disease occurs, i.e., a benefit inferred from the mitogenic and motogenic (wound healing) effects observed in cell culture and murine models of colitis. The cell protective, mitogenic and motogenic effects of AMP77-97 peptide also result in a therapeutic role in cancer-therapy induced mucositis of the GI tract as often occurs during chemotherapy and/or radiation therapy. Mucositis occurs in this setting because the therapeutic protocol is designed to destroy proliferating cancer cells, but may also damage rapidly growing cells that line the mouth, throat, or GI mucosa at any point along its entire length. Injury and/or destruction of the protective mucosal epithelium can result in life-threatening infection which puts the patient at risk for gut-derived sepsis and death. Evidence has been obtained in mice and cell culture which suggests therapeutic benefits of AMP77-97 peptide in the treatment of gut-derived sepsis (cell protection), gastritis and gastric ulcers (cell protection, mitogenesis, restitution), and infection with *H. pylori* (growth inhibition of the organism) in humans. The mitogenic and cell protective effects of AMP77-97 peptide on renal epithelial cells (MDCK line) in culture disclosed herein also predict therapeutic role for the peptide in patients with acute renal failure. In summary, the cell protective, mitogenic, and motogenic effects of AMP77-97 peptide and recombinant human AMP-18 (rhAMP-18) offer multiple therapeutic strategies to prevent and/or limit disruption of epithelial barrier function and structure, and also speed regeneration after mucosal injury in gut and kidney.

Example 4

Mitogenic and Motogenic Effects of AMP77-97 Peptide in Cell Culture Support a Therapeutic Role in Gastric Mucosal Injury The synthesis of AMP-18 is confined to lumenal mucosal lining epithelial cells of the gastric antrum of humans and other mammals. Inside cells the protein is co-localized with mucins in secretion granules, and appears to be secreted into the mucus overlying the apical plasma membrane. Recombinant human AMP-18 prepared in *E. coli* exerts its mitogenic effect at a concentration an order of magnitude lower than growth-promoting synthetic peptides derived from the center of the mature protein. Peptide 77-97, the most potent mitogenic AMP-derived peptide identified to date, is amino acid sequence-specific, and appears to be cell-type specific as it does not stimulate growth of fibroblasts or HeLa cells. Mitogenesis by specific AMP77-97 peptides appears to be mediated by a cell surface receptor because certain peptides that are not active mitogens can competitively inhibit, in a concentration-dependent manner, the growth-stimulating effects of peptide 58-99 and antrum cell extracts. AMP-18 and its derived peptides exhibit diverse effects on stomach and intestinal epithelial cells making it likely they play a critical role in repair after gastric mucosal injury. These include mitogenesis, restitution, maturation of barrier function, and cell protection after oxidant, non-steroidal anti-inflammatory (NSAID), and DSS-mediated injury. Certain of these physiological effects can occur at concentrations that are relatively low for rhAMP-18 (<50 µM) compared to the concentrations of other gastric peptide mediators such as trefoil peptides or the α-defensin, cryptdin 3 (>100 µM). Immunoreactive AMP-18 is apparently released by cells of the mouse gastric antrum after indomethacin gavage, and by canine antrum cells in primary culture exposed to forskolin, suggesting that the protein is subject to regulation. AMP-18 likely plays a role in physiological and pathological processes such as wound healing in the gastric mucosal epithelium in vivo as may occur in gastritis secondary to NSAID drugs, other pharmaceutical agents and alcohol, ulcer disease, and the consequences of *H. pylori* infection and inflammation.

Materials and Methods

Localization of AMP-18: The antisera to AMP-18 have proven to be excellent histochemical probes, reacting strongly with sections of the mouse gastric antrum region but not with tissue from the gastric fundus, duodenum or intestine, confirming the results of the immunoblots. The preimmune sera give negligible reactions even at much higher concentration. The AMP-18 protein appears to be concentrated in mucosal epithelial cells lining the stomach lumen, although lesser signals in cells deeper in the tissue and along the upper crypt regions suggest that cells may begin to express the protein as they migrate toward the lumenal layer. Higher magnification of the histochemical preparations indicates only a general cytoplasmic staining at this level of resolution; there are some patches of intense staining that may be the light microscope equivalent of granule-packed regions of some lumenal surface cells seen by electron microscopy (EM). The localization of AMP-18 in the antrum mucosa is therefore very different from those cells synthesizing gastrin which are deep in the mucosal layer.

Growth factor activity on epithelial cell cultures: A function for AMP-18 is that it is a growth factor at least partly responsible for the maintenance of a functional mucosal epithelium in the pyloric antrum and possibly elsewhere in the stomach. Initially, stomach epithelial cell lines were not immediately available, but kidney epithelial cell systems (Kartha et al., 1992; Aithal et al., 1994; Lieske et al., 1994) were used. A fractionated antrum mucosal cell extract was used for these experiments. Using immunoblotting as a probe to follow fractionation, on lysis of the mucosal cells scraped from either pig or mouse antrum, the AMP-18 antigen was recovered in the 35S fraction on sucrose density gradients. Such high speed supernatant fractions served as the starting material for studies on cell growth. Unexpectedly, these extracts stimulated a 50% increase in confluent renal epithelial cells of monkey (BSC-1 cells), but had no effect on HeLa or WI-38 fibroblast cells. The stimulation of BSC-1 cells was at least as effective as that observed with diverse polypeptide mitogens, including EGF, IGF-I, aFGF, bFGF and vasopressin, assayed at their optimal concentrations. Comparable growth stimulation by the antrum extracts was observed when DNA synthesis was assessed by measuring [$^3$H]thymidine incorporation into acid-insoluble material. The biological activity of the antrum extracts survived heating for 5 minutes at 65° C., and dialysis using a membrane with $M_r$ cutoff of 10 kDa, which would eliminate most oligopeptides; this treatment removes 60-70% of polypeptide material, but spared AMP-18 as assayed by immunoblots. More importantly, mitogenic stimulation of BSC-1 cells by the mouse or pig antrum extract was inhibited when either of two different antisera to the human recombinant preAMP-18 that includes the signal peptide sequence (expressed in *E. coli*) was added to the culture medium. Preimmune sera (1:100 to 1:800) had no effect on cell growth, nor did they alter the mitogenic effect of the antrum extracts. These observations suggest that gastric mucosal cell AMP-18 functions as a potent mitogen for kidney epithelial cells, which do not normally express this protein.

To gain further evidence that the growth-promoting activity in the partially fractionated antrum extracts was mediated by the AMP-18 protein, an aliquot of the mouse extract was subjected to SDS-polyacrylamide gel electrophoresis; the method used previously to determine the N-terminal sequence of the natural protein. The gel was cut into 2-mm slices and each slice was extracted with 3% acetonitrile in phosphate-buffered saline containing 1% BSA. The extract supernatants were assayed for mitogenic activity. The results indicated that one slice containing protein in the 16-19 kDa range possessed growth-promoting activity. Significantly, this growth response was blocked by the immune but not the pre-immune sera. Taken together with the relatively low sedimentation rate of the protein, these findings provide additional evidence to support the conclusion that AMP-18 is an epithelial cell mitogen and that it functions as a monomer or possibly a homotypic dimer. It also implies that the structure of the protein is such that it can readily reacquire a native conformation after the denaturing conditions of SDS-gel electrophoresis.

To assess the interaction of the antrum growth factor activity with other cytokines, its activity was tested to determine if it was additive with EGF in epithelial cell cultures. EGF (50 ng/ml) added with untreated mouse antrum extract (10 µg/ml), or heated, dialyzed pig extract (10 µg/ml) exhibited additive stimulation of mitogenesis; up to 74% increase in cell number above the quiescent level; the greatest stimulation observed so far for any factor using the BSC-1 cell assay. This observation suggests that AMP-18 and EGF initiate proliferation by acting on different cell surface receptors. It also implies that AMP-18 growth factor activity might normally collaborate with other autocrine and paracrine factors in the maintenance or restitution of the epithelium. In view of the results with EGF, it is likely that AMP-18 is secreted at and possibly acts upon the apical face (i.e., stomach lumenal face) of the epithelial cell layer while other factors (for which EGF may serve as an example) act from the basal surface.

Expression of recombinant protein. *E. coli*. Recombinant constructs are generally engineered by polymerase-chain-reactions using synthetic oligonucleotides complementary to the appropriate regions of the full-length cDNA sequences within the PT/CEBP vector and extended by convenient restriction enzyme sites to enable ready insertion into standard vector polylinkers. The initial experiments with expression of the AMP open reading frame (ORF) in bacterial systems employed an expression vector PT/CEBP, which included an N-terminal His6-tag (SEQ ID NO: 9) (Jeon et al., 1994), intended to facilitate the purification of the expressed protein on nickel ($Ni^{2+}$)-NTA resin (Qiagen). Expression of the full-length human cDNA within this vector in the host BL21(DE3)pLyS gave good yields of insoluble protein, which after electrophoresis under denaturing conditions was suitable for use as an immunogen in rabbits to obtain specific high-titer antibodies, but which has not been useful for analysis of the protein's native structure and function. This insolubility is most probably due to the presence of an unnatural N-terminus, having a His6-tag (SEQ ID NO: 9) upstream of hydrophobic signal peptide, in the expressed protein. Engineering vectors which will express the ORF without the hydrophobic signal peptide sequence are also useful. These are constructed using bacterial expression vectors with and without N- or C-terminal His-tags. The human AMP-18 sequence lacking the 20 amino acid signal peptide and containing a His6-tag (SEQ ID NO: 9) was also expressed in bacteria.

*Pichia pastoris*. Among the simple eukaryotes, the budding yeast *P. pastoris* is useful as an expression system for production and secretion of functional recombinant proteins (Romanos et al., 1992; Cregg et al., 1993). In this system, secretion of the foreign protein may utilize either its own signal peptide or the highly compatible yeast mating-type alpha signal. This organism will correctly process and secrete and at least partially modify the AMP-18 protein. Vectors for constitutive and regulated expression of foreign genes are developed in *Pichia* (Sears et al., 1998). In addition to a poly-linker cloning site, these vectors contain either the high expression constitutive glyceraldehyde-3-phosphate dehydrogenase (GAP) or the methanol-regulated alcohol oxidase promoter (AOX1). The latter is an extremely stringent promoter yielding insignificant product in normal culture conditions while giving the highest expression of the vectors tested in the presence of methanol, amounting to as much as 30% of the cell protein. The advantage that the yeast *Pichia* has over the mammalian and insect alternatives is that it is continuously grown in protein-free media, thus simplifying the purification of the expressed protein and eliminating extraneous bioactivities originating in the serum or the host animal cells. A pIB4 construct (inducible by methanol-containing medium) contains the complete human preAMP-18 cDNA sequence.

Baculovirus/insect cells. An alternative, frequently successful, non-mammalian eukaryotic expression system is that using recombinant Baculovirus, such as *Autographa californica*, in an insect cell culture system. As with *Pichia*, a large repertoire of convenient vectors are available in this system, containing both glutathione S-transferase (GST)- and His6-tags (SEQ ID NO: 9) (Pharmingen). Transfections are carried out into *Spodoptera frugiperda* (Sf) cells; these cells can be slowly adapted to protein-free medium to favor the purification of secreted proteins. If an endogenous signal peptide does not function in these cells, secretion of foreign proteins can also be forced using vectors containing the viral gp67 secretion signal upstream of the cloning site. Recombinant proteins can be expressed at levels ranging from 0.1-50% total cell protein. Some protein modifications may be more favored in this insect cell system relative to yeast, but still may not duplicate the mammalian system. It appears that the insect expression system would be somewhat more onerous than *Pichia*, and not entirely substitute for expression in mammalian cells. The human AMP-18 sequence lacking the 20 amino acid signal peptide and containing a His6-tag (SEQ ID NO: 9) was expressed in Baculovirus.

Mammalian cells. Modifications not detectable by immunoblot analysis may take place in mammalian cells that are not duplicated in cells of other eukaryotes. Although not as convenient as prokaryotic and simple eukaryotic systems, mammalian cells are now frequently used for both transient and continuous expression of foreign proteins. Several growth factors have been expressed and secreted in significant amounts using these systems.

The plasmid pcDNA3/human kidney 293 system: pcDNA3 contains a polylinker cloning site flanked by the strong constitutive cytomegalovirus (CMV) promoter and a SV40 polyA signal (Invitrogen). Laboratory experience is that 60-90% transient transfection levels can be achieved. To this end, PCR amplification of the human preAMP cDNA clone is performed with oligonucleotides that contain the initiation codon and native ribosome binding site (Kozak sequence) as well as suitable restriction enzyme linkers for correct orientation into pcDNA3. Favorable constructs were identified in the transient assay using the potent antibiotic blasticidin S and a vector containing the resistance gene, stable mammalian transfectant cell lines can be established "in less than one week" (Invitrogen). The available vectors also include the constitutive CMV promoter, a polylinker cloning site, an elective V5-epitope/His6-tag (SEQ ID NO: 9) and the SV40 poly(A) signal (PcDNA6/V5-His).

Expression and analysis of altered (modified) forms of AMP-18: Given an efficient expression system for the production of "wild-type" AMP-18, a series of mutant proteins, containing either deletions or substitutions may be created, which permit analysis of the functional domains. The amphipathic helices, the conserved cystine (C) residues and the basic amino acids doublets, which may be cleavage sites, are attractive targets. Although not as simple as an enzyme assay, the mitogenesis assay is routine and replicable, and enables "mutants" to be characterized as fast as they are constructed. Dominant negative (or positive) "mutants" are as significant as mutations exhibiting simple loss of function, because these imply interactions with other factors including possible cell receptors.

Biochemical and immunoaffinity fractionation of expressed and native gastrokine proteins: In the case of some of the expressed forms of AMP-18, the recombinant protein contains peptide tags that will permit the rapid purification of soluble protein. The presence of these tags, if they do not severely interfere with the protein's normal functions, also permit analysis of interactions with other relevant macromolecules. His6-tags (SEQ ID NO: 9) permit purification by binding the recombinant proteins to Ni-NTA resin beads (Janknecht et al., 1991; Ni-NTA resin from Qiagen). The tagged protein is bound with greater affinity than most antigen-antibody complexes and can be washed rigorously before the $N_i^{2+}$-histidine chelation complex is disrupted by excess imidazole to release the purified protein. GST-tagged recombinant proteins are purified on glutathione-agarose, washed and then eluted with reduced glutathione (Smith and Johnson, 1988). As with all the proposed expression systems, each protein preparation may be tested at the earliest possible stage for its growth factor activity.

Conventional fractionation procedures are used to achieve the desired purity, particularly in the case of the isolation of the natural protein from tissue. Pig antrum mucosa is a preferred starting point for the latter, using initial centrifugation and heat-treatment protocol, followed by a size-exclusion column: BioGel P60 is suitable, given the evidence that the 18 kDa protein exists, most probably as a monomer in the extracts. The eluant is loaded on an immunoaffinity matrix created by crosslinking anti-AMP antibodies purified on HiTrap Protein A to CNBr-activated Sepharose 4B (Pharmacia). Further modification of the immunoaffinity matrix may be helpful, either by extension of the linker to the matrix, which has proven useful in the past (Aithal et al., 1994), or by crosslinking the antibody to immobilized protein-A. Because active protein can be recovered by SDS-gel elution, active protein may also be recovered from the antigen-antibody complexes. Further fractionation could be achieved by C8 reversed-phase high-performance liquid chromatography (HPLC) column. A final step is the use of the SDS-gel elution technique with confirmation of identity by N-terminal sequencing. In all of these steps the immunodetectable AMP-18 and the growth factor activity should fractionate together.

AMP-18 related synthetic peptides: AMP-18 may be precursor to one or several bioactive peptides. Synthetic peptides provide a convenient avenue to explore the function of a protein; peptides may mimic aspects of the function or antagonize them. If a peptide either duplicates or inhibits the protein's activity, then it suggests the identity of functional domains of the intact protein, and also provides the possibility of synthesizing specifically tagged probes to explore protein-cell interactions.

The possible inclusion of D-amino acids in the peptides (in normal or reverse order) may stabilize them to degradation while permitting retention of biological function. Further the ability to synthesize active peptides enables tags that facilitate studies of the nature, tissue distribution and number of cellular receptors. Such tags include His-6 biotin or iodinated tyrosine residues appended to the peptide sequence (several of the bioactive peptides have a naturally occurring tyrosine at the C-terminus).

Synthetic peptides that can be locked in the helical form by lactam bridges (Houston et al., 1996) enhanced biological activity; at least one pair of appropriate acidic and basic amino acid residues for lactam formation already exist in potential helix regions of AMP-18.

Interactions of AMP-18 and related peptides with cells: assessment of cell growth: Non-transformed monkey kidney epithelial cell line BSC-1 and other epithelial cell lines were used to assess effects on growth. In general, conditions were chosen for each line such that cells are grown to confluence in plastic dishes in supplemented growth medium with minimal calf (or fetal) serum for growth (Lieske et al., 1997); BSC-1 cells become confluent at 106/60-mm dish with 1% calf serum. At the start of the growth assay the medium on the confluent culture was aspirated and replaced with fresh medium with minimal serum to maintain viability (0.01% for BSC-1) cells. AMP-18 preparations were added to the culture medium and 4 days later the cell monolayer was rinsed, detached with trypsin, and the cells were counted using a hemocytometer. Determination of the capacity of AMP-18 to initiate DNA synthesis was measured by the incorporation of [$^3$H]thymidine (Toback, 1980); to confirm the DNA synthesis assay, autoradiograms of leveled cells were counted (Kartha and Toback, 1985).

The protein AMP-18 is expressed in the antrum mucosa and to a lesser extent in the adjacent corpus mucosa. However, both antrum extracts and the active synthetic peptides stimulate proliferation of most simple epithelial cell lines. The major criterion used, apart from cells which might be natural targets for AMP-18 or its peptides, was that of growth control, particularly cell-density restriction. Many transformed stomach lines derived from human cancer patients are available from various sources, but most of these do not exhibit growth control. For example, a gastric AGS adenocarcinoma cell subline from Dr. Duane Smoot (Howard University College of Medicine) showed a greater degree of contact inhibition, and responded well to AMP-18 and its derived peptides. These cells do not naturally synthesize AMP-18. Similar responses were observed with the non-transformed rat IEC intestinal epithelial cells (provided by Dr. Mark Musch, Dept. Medicine, University of Chicago); the latter show excellent epithelial cell characteristics in culture (Quaroni et al., 1979; Digass et al., 1998).

Bio-Models for evaluating treatment of mucositis: Effects of AMP-18 derived peptides on model systems were performed as described in Alvarez et al. (2003). The methods and design of experiments are summarized herein.

Acute Radiation-induced Mucositis. Oral mucositis was induced in hamsters by administering a single dose of radiation of 40 Gy. On day 0, under anesthesia (intraperitoneal injection of ketamine [160 mg/kg] and xylazine [8 mg/kg]), the left buccal pouch was everted, fixed, and radiated while the rest of the animal was shielded with lead cover. Radiation was generated using a 160-kV potential (18.75-ma) source at a focal distance of about 21 cm, hardened with a 3-mm Al filtration system. Ionizing radiation was targeted at the left buccal pouch mucosa at a rate of 1.32 Gy/minute.

AMP-derived peptide in phosphate-buffered saline (PBS) was administered at 0 to 80 mg/kg by daily subcutaneous injection starting five days before (day −5) radiation, and 15 days afterwards (day +15) A control group consisted of irradiated animals dosed with vehicle (PBS) on days −5 to +15. Neither AMP77-97 peptide or vehicle was given on the day radiation was administered. Using the dosing schedule described above, different amounts of AMP peptide were administered before and after administration of radiation to define an optimal dosing schedule for AMP-18-derived peptides in this acute radiation induced model of mucositis in the hamster cheek pouch.

Mucositis Evaluation: The progression of mucositis was monitored daily for both models. Every other day starting on day 6 postirradiation, animals were anesthetized using inhalation anesthesia, and the left buccal pouch was everted and photographed. At the conclusion of the study's clinical phase, film was developed, and resulting photos were randomly numbered and then scored in blinded fashion by two observers. A 0-5 scoring system was used that applied the following numerical score to buccal lesions: 0, normal mucosa; 1, erythema and vasodilation; 2, severe erythema and vasodilation, with erosion of superficial aspects of mucosa leaving denuded areas with decreased stippling of mucosa. 3, severe erythema, vasodilation, and formation of ulcers in one or more places. Cumulative size of ulcers involved 25% of the pouch mucosa. Pseudomembrane formation is evident. 4, severe erythema and vasodilation. Cumulative size of ulcers involved about half of the pouch mucosa. Loss of mucosal pliability. 5, diffuse, extensive ulceration. Loss of pliability, pouch can only partially be extracted from mouth; see FIG. 5. The reported scores represent the average of the observations from the two blinded observers. In this model, a score of 3 coincides with a clinically significant National Cancer Institute or WHO score 3. Severity of oral mucositis (OM) was calculated using the scores per treatment group on each observation day (mean±SE). Using the severity scores, results are also represented as percentage of days with a score of three or above.

Human AMP-18 Sequences
Amino acid sequence of human AMP-18

```
                                              (SEQ ID NO: 7)
MKFTIVFAGL LGVFLAPALA NYNIDVNDDN NNAGSGQQSV

SVNNEHNVAN VDNNNGWDSW NSIWDYGNGF AATRLFQKKT

CIVHKMNKEV MPSIQSLDAL VKEKKLQGKG PGGPPPKGLM

YSVNPNKVDD LSKFGKNIAN MCRGTPIYMA EEMQEASLFF

YSGTCYTTSV LWIVDISFCG DTVEN
```

Amino acids 77-97 (LDALVKEKKLQGKGPGGPPPK) (SEQ ID NO: 6) are highlighted by double underlines. The amino acid positions correspond to the mature protein. The first twenty amino acids correspond to the signal peptide and is shown by a single underline.

The cDNA sequence of human AMP-18 sequence (the coding sequence runs from 44-601) is shown below.

```
                                                                (SEQ ID NO: 8)
  1    catgcttgcc tactcctctg tccactgctt tcgtgaagac aagatgaagt tcacaattgt 61    ctttgctgga cttcttggag tctttctagc tcctgcccta gctaactata atatcgacgt 121    caatgatgac aacaacaatg ctggaagtgg gcagcagtca gtgagtgtca acaatgaaca 181    caatgtggcc aatgttgaca ataacaacg atgggactcc tggaattcca tctgggatta 241    tggaaatggc tttgctgcaa ccagactctt tcaaaagaag acatgcattg tgcacaaaat 301    gaacaaggaa gtcatgccct ccattcaatc ccttgatgca ctggtcaagg aaaagaagct 361    tcagggtaag ggaccaggag gaccacctcc caagggcctg atgtactcag tcaacccaaa 421    caaagtcgat gacctgagca agttcggaaa aaacattgca aacatgtgtc gtgggattcc 481    aacatacatg gctgaggaga tgcaagaggc aagcctgttt ttttactcag gaacgtgcta 541    cacgaccagt gtactatgga ttgtggacat ttccttctgt ggagacacgg tggagaacta 601    aacaatttt taaagccact atggatttag tcatctgaat atgctgtgca gaaaaaatat 661    gggctccagt ggtttttacc atgtcattct gaaattttc tctactagtt atgtttgatt 721    tctttaagtt tcaataaaat catttagcat tgaattca
```

DOCUMENTS CITED

The following documents are incorporated by reference to the extent they relate to or describe materials or methods disclosed herein.

Aithal, N. H., et al. (1994) *Am. J. Physiol.* 266:F612-619.
Alvarez et al. (2003), *Clin. Can. Res.* 9: 3454-3461.
Ausubel, et al. (1993), Current Protocols In Molecular Biology, John Wiley & Sons, New York, N.Y., 1993.
Baczako, K, et al. (1995) *J. Pathol.* 176:77-86.
Blaser, M. J. et al. (1987) *Gastroenterol.* 93:371-383
Boman, H. G. (1995) *Ann. Rev. Immunol.* 13:61-92.
Cohen, G. B., et al. (1995) *Cell* 80:237-248.
Cregg, J. M., et al. (1993) *Bio/Technol.* 11:905-910.
Dignass, A. U., et al. (1998) *Eur. J. clin. Invest.* 28:554-561
Falk, P., et al. (1993) *Proc. Nat. Acad. Sci.* 90:2035-2039.
Farrell, C. L., et al (1999) *Int. J. Radiat. Biol.* 75(5): 609-620.
Geum, D., et al. (2002) *J. Biol. Chem.* 277:19913-19921.
Goodwin, C. S., et al., (1986) *J. Clin. Microbiol.* 39:353-356.
Hasty, P., et al. (1991) *Mol. Cell. Biol.* 11:5586-5591.
Houston, M. E., et al. (1996) *Biochem.* 35:10041-10050.
Huot, J., et al. (1996) *Cancer Res.* 56:273-279.

Janknecht, R., et al. (1991) *Proc. Nat. Acad. Sci. USA* 88:8972-8976
Jeon, C. J., et al. (1994) *Proc. Nat. Acad. Sci. USA* 91:9106-9110
Johnson, F. R. and McMinn, R. M. H. (1970) *J. Anat.* 107: 67-86.
Kartha, S. and Toback, F. G. (1985) *Am. J. Physiol.* 249:F967-F972
Kartha, S., et al. (1992) *Exp. Cell Res.* 200:219-226.
Knoxx J J, et al. (2000) *Drugs Aging* 17(4):257-67.
Kucharzik, T., et al (2001) *Am. J. Pathol.* 159:2001-2009.
Laughlin, R. S., et al. (2000) *Ann. Surg.* 232:133-142.
Lavoie, J. N., et al. (1993) *J. Biol. Chem.* 268: 3420-3429.
Lavoie, J. N. et al. (1995) *Mol. Cell. Biol.* 15:505-516.
Lieske, J. C., et al. (1994) *Proc. Natl. Acad. Sci.* 91:6987-6991.
Lieske, J. C., et al. (1997) *Am. J. Physiol.* F224-F233.
Lacy, E. R. (1998) *J. Clin. Gastroenterol.* 10 (Suppl 1):72-77.
Madara, J. L. et al. (1986) *J. Cell Biol.* 102:2125-2136.
Mansour, S., et al. (1988) *Nature* 336:348.
Moore, K. S., et al. (1991) *J. Biol. Chem.* 266:19851-19857.
Musch M. W., et al. (1996) *Am. J. Physiol* 270:C429-C436.
Nguyen, J. T., et al. (1998) *Science* 282:2088-2092.
Nomura, A., et al. (1991) *N. Engl. J. Med.* 325-1132-1136.
Nusrat, A., et al. (1992) *J. Clin. Invest.* 89:1501-1511.
Park, C. B., et al. (1997) *FEBS Lett.* 411:173-178.
Parsonnet, J., et al. (1991) *N. Engl. J. Med.* 325:1127-1131.
Peterson D E (1999) *Curr. Opin. Oncol* 11 (4):261-6.
Plevova P. (1999) *Oral Oncol;* 35(5):453-70.
Podolsky, D. K. (1997) *J. Gastroenterol.* 32:122-126.
Powell, C. J., (1987) Ph.D. Dissertation, University of Chicago.
Quaroni, A., et al. (1979) *J. Cell Biol.* 80:248-265.
Remington's Pharmaceutical Sciences, 20th Edition, A. R. Gennaro (Williams and Wilkins, Baltimore, Md., 2000)
Romanos, M. A., et al. (1992) *Yeast* 8:423-488.
Rotimi, V. O., et al. (1990) *Afr. J. Med. med. Sci.* 19:275-280.
Sands, B. E. and Podolsky, D. K. (1996) *Ann. Rev. Physiol.* 58:253.
Schlessinger, J. and Ullrich, A. (1992) *Neuron* 9:383-391.
Sears, I. B., et al. (1998) *Yeast* 14.
Sonis S T, et al. (2001) *J Clin-Onco* 19(8):220 1-5.
Segarini, P. R., et al. (1987) *J. Biol. Chem.* 262:14655-14662.
Smith, D. B. and Johnson, K. S. (1988) *Gene* 67:31-40.
Suzuki, A., et al. (2001) *J. Cell Biol.* 152:1183-1196.
Toback, F. G. (1980) *Proc. Nat. Acad. Sci.* 77:6654-6656.
Wong, V. (1997) *Am. J. Physiol.* 273:C1859-C1867.
Yarden et al. and Ullrich (1988) *Biochemistry* 27:3113-3119.
Yoo, O. J. et al. (1982) *PNAS* 79:1049-1053.

The invention claimed is:

1. A method to reduce or delay the onset of oral mucositis, the method comprising administering a pharmaceutical composition comprising a therapeutically effective amount of a fragment of the AMP-18 protein (SEQ ID NO: 7) and a pharmaceutically acceptable carrier, wherein the protein fragment comprises an amino acid sequence KKLQGKGPGGPPPK (SEQ ID NO: 2) and wherein the protein fragment delays the onset, or reduces the intensity or duration of oral mucositis or a combination thereof.

2. The method of claim 1, wherein the protein fragment comprises an amino acid sequence LDALVKEKKLQGKGPGGPPPK (SEQ ID NO: 6).

3. The method of claim 1, wherein administering the pharmaceutical composition is selected from oral administration, intravenous administration, subcutaneous administration, topical administration, transdermal administration, intraperitoneal administration, transmucosal administration and nasal administration.

4. The method of claim 3, wherein the administration is topical.

5. The method of claim 1, wherein the oral mucositis is induced by a therapy to treat cancer.

6. The method of claim 5, wherein the cancer therapy is radiation therapy.

7. The method of claim 5, wherein the cancer therapy is chemotherapy.

8. The method of claim 5, wherein the therapy is a combination of radiation and chemotherapy.

9. The method of claim 1, wherein the protein fragment is a synthetic peptide.

10. A method to treat oral mucositis, the method comprising:
    (a) obtaining a pharmaceutical composition comprising a therapeutically effective amount of a synthetic peptide consisting of an amino acid sequence LDALVKEKKLQGKGPGGPPPK (SEQ ID NO: 6) and a pharmaceutically acceptable carrier; and
    (b) administering the pharmaceutical composition to treat oral mucositis.

11. The method of claim 10, wherein the mucositis is cancer therapy induced.

* * * * *

```
SEQUENCE LISTING

<160> NUMBER OF SEQ ID NOS: 9

<210> SEQ ID NO 1
<211> LENGTH: 42
<212> TYPE: PRT
<213> ORGANISM: Homo sapiens

<400> SEQUENCE: 1

Lys Lys Thr Cys Ile Val His Lys Met Lys Lys Glu Val Met Pro Ser
 1               5                  10                  15

Ile Gln Ser Leu Asp Ala Leu Val Lys Glu Lys Lys Leu Gln Gly Lys
            20                  25                  30

Gly Pro Gly Gly Pro Pro Pro Lys Gly Leu
        35                  40

<210> SEQ ID NO 2
<211> LENGTH: 14
<212> TYPE: PRT
<213> ORGANISM: Homo sapiens

<400> SEQUENCE: 2

Lys Lys Leu Gln Gly Lys Gly Pro Gly Gly Pro Pro Pro Lys
 1               5                  10

<210> SEQ ID NO 3
<211> LENGTH: 18
<212> TYPE: PRT
<213> ORGANISM: Homo sapiens

<400> SEQUENCE: 3

Lys Lys Leu Gln Gly Lys Gly Pro Gly Gly Pro Pro Pro Lys Gly Leu
 1               5                  10                  15

Met Tyr

<210> SEQ ID NO 4
<211> LENGTH: 25
```

```
<212> TYPE: PRT
<213> ORGANISM: Homo sapiens

<400> SEQUENCE: 4

Leu Asp Ala Leu Val Lys Glu Lys Lys Leu Gln Gly Lys Gly Pro Gly
 1               5                  10                  15

Gly Pro Pro Pro Lys Gly Leu Met Tyr
                20                  25

<210> SEQ ID NO 5
<211> LENGTH: 23
<212> TYPE: PRT
<213> ORGANISM: Mus musculus

<400> SEQUENCE: 5

Leu Asp Thr Met Val Lys Glu Gln Lys Gly Lys Gly Pro Gly Gly Ala
 1               5                  10                  15

Pro Pro Lys Asp Leu Met Tyr
                20

<210> SEQ ID NO 6
<211> LENGTH: 21
<212> TYPE: PRT
<213> ORGANISM: Homo sapiens

<400> SEQUENCE: 6

Leu Asp Ala Leu Val Lys Glu Lys Lys Leu Gln Gly Lys Gly Pro Gly
 1               5                  10                  15

Gly Pro Pro Pro Lys
                20

<210> SEQ ID NO 7
<211> LENGTH: 185
<212> TYPE: PRT
<213> ORGANISM: Homo sapiens

<400> SEQUENCE: 7

Met Lys Phe Thr Ile Val Phe Ala Gly Leu Leu Gly Val Phe Leu Ala
 1               5                  10                  15

Pro Ala Leu Ala Asn Tyr Asn Ile Asp Val Asn Asp Asp Asn Asn Asn
                20                  25                  30

Ala Gly Ser Gly Gln Gln Ser Val Ser Val Asn Asn Glu His Asn Val
            35                  40                  45

Ala Asn Val Asp Asn Asn Gly Trp Asp Ser Trp Asn Ser Ile Trp
         50                  55                  60

Asp Tyr Gly Asn Gly Phe Ala Ala Thr Arg Leu Phe Gln Lys Lys Thr
 65                  70                  75                  80

Cys Ile Val His Lys Met Asn Lys Glu Val Met Pro Ser Ile Gln Ser
                85                  90                  95

Leu Asp Ala Leu Val Lys Glu Lys Lys Leu Gln Gly Lys Gly Pro Gly
                100                 105                 110

Gly Pro Pro Pro Lys Gly Leu Met Tyr Ser Val Asn Pro Asn Lys Val
                115                 120                 125

Asp Asp Leu Ser Lys Phe Gly Lys Asn Ile Ala Asn Met Cys Arg Gly
                130                 135                 140

Ile Pro Thr Tyr Met Ala Glu Glu Met Gln Glu Ala Ser Leu Phe Phe
145                 150                 155                 160

Tyr Ser Gly Thr Cys Tyr Thr Thr Ser Val Leu Trp Ile Val Asp Ile
                165                 170                 175
```

```
Ser Phe Cys Gly Asp Thr Val Glu Asn
            180                 185

<210> SEQ ID NO 8
<211> LENGTH: 758
<212> TYPE: DNA
<213> ORGANISM: Homo sapiens

<400> SEQUENCE: 8
catgcttgcc tactcctctg tccactgctt tcgtgaagac aagatgaagt tcacaattgt      60
ctttgctgga cttcttggag tctttctagc tcctgcccta gctaactata atatcgacgt     120
caatgatgac aacaacaatg ctggaagtgg gcagcagtca gtgagtgtca acaatgaaca     180
caatgtggcc aatgttgaca ataacaacgg atgggactcc tggaattcca tctgggatta     240
tggaaatggc tttgctgcaa ccagactctt tcaaaagaag acatgcattg tgcacaaaat     300
gaacaaggaa gtcatgccct ccattcaatc ccttgatgca ctggtcaagg aaaagaagct     360
tcagggtaag ggaccaggag gaccacctcc caagggcctg atgtactcag tcaacccaaa     420
caaagtcgat gacctgagca agttcggaaa aaacattgca aacatgtgtc gtgggattcc     480
aacatacatg gctgaggaga tgcaagaggc aagcctgttt ttttactcag aacgtgcta     540 cacgaccagt gtactatgga ttgtggacat ttccttctgt ggagacacgg tggagaacta     600
aacaattttt taaagccact atggatttag tcatctgaat atgctgtgca gaaaaaatat     660
gggctccagt ggttttacc atgtcattct gaaattttc tctactagtt atgtttgatt       720
tctttaagtt tcaataaaat catttagcat tgaattca                             758

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 9

His His His His His His
1               5
```